US010414664B2

(12) United States Patent
Gounder et al.

(10) Patent No.: US 10,414,664 B2
(45) Date of Patent: Sep. 17, 2019

(54) PROCESS FOR PRODUCING MATERIALS HAVING A ZEOLITE-TYPE FRAMEWORK WITH HETEROATOMS INCORPORATED THEREIN

(71) Applicant: PURDUE RESEARCH FOUNDATION, West Lafayette, IN (US)

(72) Inventors: Rajamani P. Gounder, Lafayette, IN (US); Juan Carlos Vega-Vila, West Lafayette, IN (US); James William Harris, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 95 days.

(21) Appl. No.: 15/686,235

(22) Filed: Aug. 25, 2017

(65) Prior Publication Data
US 2018/0057364 A1 Mar. 1, 2018

Related U.S. Application Data

(60) Provisional application No. 62/380,739, filed on Aug. 29, 2016.

(51) Int. Cl.
*C01B 39/06* (2006.01)
*B01J 29/04* (2006.01)
(Continued)

(52) U.S. Cl.
CPC ............ *C01B 39/06* (2013.01); *B01J 29/04* (2013.01); *B01J 29/046* (2013.01); *B01J 29/047* (2013.01);
(Continued)

(58) Field of Classification Search
CPC ..... C01B 39/026; C01B 39/06; C01B 39/065; B01L 29/061; B01L 29/7007;
(Continued)

(56) References Cited

U.S. PATENT DOCUMENTS 5,098,687 A * 3/1992 Skeels ............... B01J 29/88
423/715
5,200,168 A * 4/1993 Apelian ............ B01J 29/7007
423/714

(Continued)

*Primary Examiner* — David M Brunsman
(74) *Attorney, Agent, or Firm* — Hartman Global IP Law; Gary M. Hartman; Domenica N.S. Hartman

(57) ABSTRACT

A process of producing a zeotype material having a zeolite-type framework. The process includes providing a zeolite having a framework, dealuminating the zeolite to remove aluminum atoms therefrom to produce a dealuminated framework comprising a plurality of vacancy sites, contacting the dealuminated framework with dichloromethane and a precursor comprising heteroatoms, and then heating the dealuminated framework, the dichloromethane, and the precursor under reflux conditions to incorporate the heteroatoms into at least some of the plurality of vacancy sites in the dealuminated framework to produce a zeotype material having a zeolite-type framework comprising the heteroatoms. In addition, a process is provided for producing a stannosilicate comprising a zeolite-type framework comprising Sn heteroatoms incorporated therein which form Sn sites in the zeolite-type framework each having an open configuration or a closed configuration. This process includes controlling relative amounts of Sn sites having open and closed configurations in the stannosilicate.

20 Claims, 13 Drawing Sheets

(51) Int. Cl.
| | |
|---|---|
| *C07H 1/00* | (2006.01) |
| *C07H 3/02* | (2006.01) |
| *B01J 29/89* | (2006.01) |
| *C01B 39/02* | (2006.01) |
| *B01J 29/70* | (2006.01) |
| *B01J 29/072* | (2006.01) |
| *B01J 29/87* | (2006.01) |
| *B01J 29/88* | (2006.01) |
| *B01J 29/06* | (2006.01) |
| *B01J 29/76* | (2006.01) |

(52) U.S. Cl.
CPC .......... *B01J 29/061* (2013.01); *B01J 29/072* (2013.01); *B01J 29/7007* (2013.01); *B01J 29/7057* (2013.01); *B01J 29/7615* (2013.01); *B01J 29/87* (2013.01); *B01J 29/88* (2013.01); *B01J 29/89* (2013.01); *C01B 39/026* (2013.01); *C01B 39/065* (2013.01); *C07H 1/00* (2013.01); *C07H 3/02* (2013.01); *B01J 2229/16* (2013.01); *B01J 2229/183* (2013.01)

(58) Field of Classification Search
CPC ............. B01L 29/86–89; B01L 29/046; B01L 29/047; B01L 29/072; B01L 29/7057; B01L 29/7615; B01L 2229/16; B01L 2229/183; C07H 1/00; C07H 3/02
See application file for complete search history.

(56) References Cited

U.S. PATENT DOCUMENTS

| | | | | |
|---|---|---|---|---|
| 5,271,761 | A * | 12/1993 | Skeels | C01B 39/065 95/116 |
| 6,063,944 | A * | 5/2000 | Di Renzo | B01J 29/89 423/713 |
| 6,759,540 | B2 * | 7/2004 | Oguchi | B01J 29/89 502/107 |
| 2005/0137436 | A1 * | 6/2005 | Ponomareva | C07C 2/66 585/422 |
| 2011/0137096 | A1 * | 6/2011 | Minoux | C07C 1/20 585/324 |

* cited by examiner

PROCESS FOR PRODUCING MATERIALS HAVING A ZEOLITE-TYPE FRAMEWORK WITH HETEROATOMS INCORPORATED THEREIN

CROSS REFERENCE TO RELATED APPLICATIONS

This application claims the benefit of U.S. Provisional Application No. 62/380,739, filed Aug. 29, 2016, the contents of which are incorporated herein by reference.

BACKGROUND OF THE INVENTION

The present invention generally relates to zeolites and materials having zeolite-type frameworks. The invention particularly relates to processes for producing silicates having zeolite-type frameworks via liquid-phase reflux procedures.

Zeolites are crystalline aluminosilicates and members of a family of microporous solids known as molecular sieves, which have the ability to selectively sort molecules based primarily on a size exclusion process. This is due to a relatively regular pore structure of molecular dimensions. As such, zeolites are commonly used as commercial adsorbents and catalysts, especially in the chemical and petrochemical industries.

Zeolites are composed of a three-dimensional framework generally comprising connected tetrahedral $[AlO_{4/2}]^-$ and $[SiO_{4/2}]$ subunits, with each subunit linked in a fourfold coordination by sharing its oxygen atoms with other such tetrahedra. Each $[AlO_{4/2}]^-$ in the framework carries a net negative charge, which is balanced by an extra-framework cation (for example, $H^+$, $K^+$, or $Na^+$). Over the course of synthesis of zeolites, the primary tetrahedral subunits are assembled into secondary building units, which are simple polyhedra such as cubes, hexagonal prisms, or cuboctahedra. The final framework structure then comprises a repeating arrangement of these secondary building units. Because there are many possibilities for the secondary building units to assemble in three dimensions, there exists a large number of crystallographically unique structures (referred to as frameworks or framework structures).

Various processes exist to replace heteroatoms that already exist in a zeolite framework with other heteroatoms in order to produce silicate molecular sieves having metal-containing zeolite-type frameworks (referred hereinafter as zeotype materials) with a variety of properties. The term heteroatom refers to elements, such as tin, titanium, zirconium, hafnium, gallium, iron, boron, germanium, beryllium, vanadium, chromium, etc., which are incorporated into the zeolite framework by partial isomorphous substitution of the typical framework heteroatoms (for example, silicon, aluminum, and phosphorus). Generally, such substitutions are intended to adjust properties of the material (e.g., Lewis acidity) for a certain application. Zeotype materials have been used for a variety of applications for chemical synthesis, pharmaceutical synthesis, and biomass conversion, including sugar isomerizations, oxidations of ketones and aldehydes, epoxidation of olefins, etc.

Current synthesis processes to prepare zeotype materials are limited in the amount of heteroatoms that can be incorporated (chemically-bonded) into the zeolite-type framework (and not just physically deposited onto the oxide surface). In addition, current processes do not allow for control over the coordination of the heteroatoms that are bonded into the framework. For example, in the case of incorporating Sn atoms into the framework to produce a stannosilicate, current applications are unable to control whether the Sn atoms form three bonds (open configuration) or four bonds (closed configuration) to the silica lattice of the framework. In many catalytic applications, only the Sn atoms that are in an open configuration are able to catalyze the reaction involved.

In view of the above, it can be appreciated that there are certain problems, shortcomings or disadvantages associated with the prior art, and that it would be desirable if a process were available for producing zeotype materials with increased amounts of heteroatoms incorporated into their zeolite-type frameworks and improved control over the configuration of heteroatom sites formed therein.

BRIEF DESCRIPTION OF THE INVENTION

The present invention provides processes suitable for producing zeotype materials having zeolite-type frameworks comprising heteroatoms incorporated therein, non-limiting examples being Sn and Ti.

According to one aspect of the invention, a process is provided that includes the steps of providing a zeolite having a framework, dealuminating the zeolite to remove aluminum atoms therefrom to produce a dealuminated framework comprising a plurality of vacancy sites, contacting the dealuminated framework with dichloromethane and a precursor comprising heteroatoms, and then heating the dealuminated framework, the dichloromethane, and the precursor under reflux conditions to incorporate the heteroatoms into at least some of the plurality of vacancy sites in the dealuminated framework to produce a zeotype material having a zeolite-type framework comprising the heteroatoms.

According to another aspect of the invention, a process is provided for producing a stannosilicate comprising a zeolite-type framework comprising Sn heteroatoms incorporated therein which form Sn sites in the zeolite-type framework each having an open configuration or a closed configuration. The process includes controlling relative amounts of Sn sites having open and closed configurations in the stannosilicate.

Other aspects of the invention include zeotype materials, stannosilicates, and titanosilicates that can be produced by the processes described above.

Technical effects of the processes described above preferably include the capability of achieving a weight loading of heteroatoms in the zeolite-type framework that is higher than currently available processes, and/or the capability of systematically controlling the coordination of heteroatom sites in the zeolite-type framework.

Other aspects and advantages of this invention will be further appreciated from the following detailed description.

DETAILED DESCRIPTION OF THE INVENTION

Figure 1:
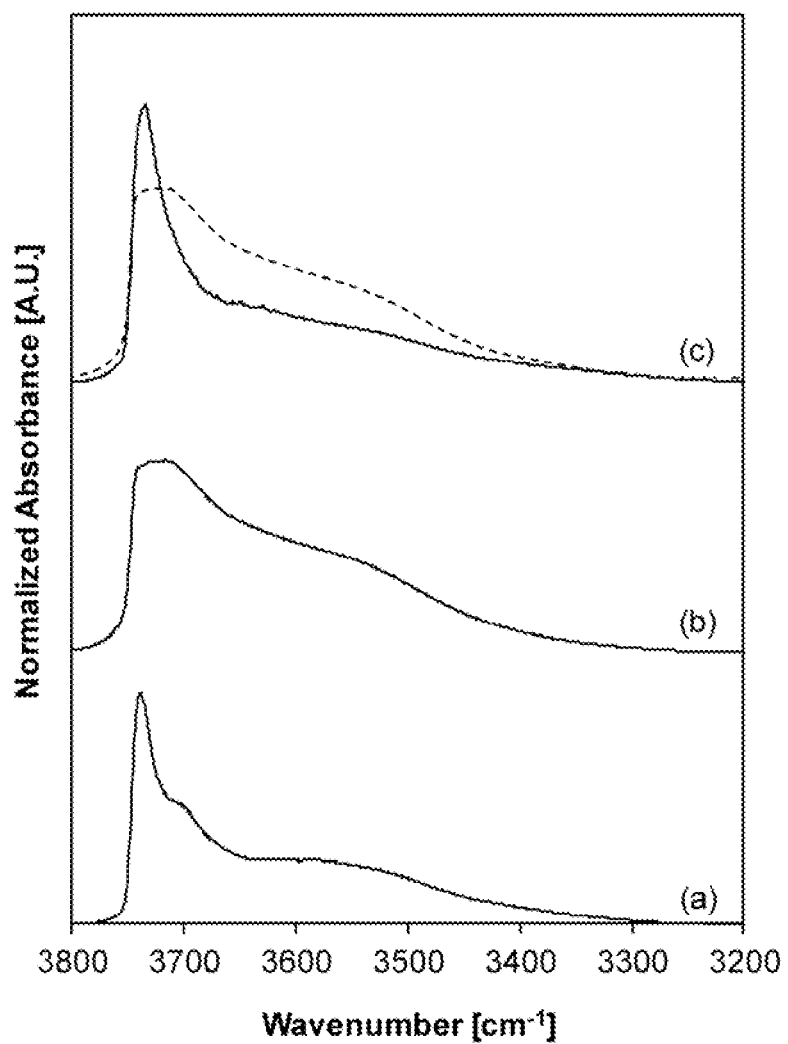
FIG. 1 includes plots of infrared (IR) spectra (303 K) collected for (a) Al-Beta-OH-54, (b) dealuminated Beta, and (c) Sn-Beta-OH-47 grafted in dichloromethane as the reflux solvent. The spectrum of dealuminated Beta (dashed line) is superimposed on (c) for comparison.

This disclosure describes processes for producing various zeotype materials by incorporating heteroatoms into vacancy sites in zeolite-type frameworks (such as but not limited to Sn, Ti, Zr, Hf, Pb, B, Ga, Fe, Be, Ge, V, Nb, Ta, Cr, Co, Cu, etc.). The heteroatoms are incorporated into the framework via a solvent that does not form hydrogen bonds with hydroxyl groups (which are present in framework vacancy sites). Nonlimiting examples of suitable solvents may include polar aprotic solvents. A specific nonlimiting example for incorporating heteroatoms is stannic chloride reflux in dichloromethane. Nonlimiting embodiments of the invention will be described in reference to experimental investigations leading up to the invention. Although the investigations predominately used Sn or Ti as the heteroatom incorporated into the zeolite-type framework, it is believed that these processes are capable of producing various zeotype materials as stated above. Further, although these investigations used samples having Beta-type zeolite frameworks, it is believed that the processes are applicable to zeolite frameworks having various other topologies.

The following describes investigations that demonstrate the ability to produce zeotype materials having Sn heteroatoms incorporated into a zeolite-type framework thereof (referred to as stannosilicates), as well as the ability to control relative amounts of open and closed configurations formed by the Sn heteroatoms at Sn sites within the framework. The processes described below are capable of achieving a weight loading of Sn in the zeolite framework that can be significantly higher that current process (for example, greater that six weight percent of Sn), and are believed to be the only known processes capable of systematically controlling the coordination of Sn sites in a zeolite-type framework.

Particular investigations compared stannosilicates produced by various liquid-phase reflux procedures to graft tin heteroatoms into vacancy sites in the zeolite-type framework (lattice). In general, Al-Beta zeolites were synthesized in either a hydroxide media (Al-Beta-OH) or a fluoride media (Al-Beta-F) with different Si/Al ratios in accordance with known practices. These Beta type zeolites were dealuminated using nitric acid in order to remove substantially all of the aluminum atoms therefrom to produce a zeolite-type framework comprising a plurality of vacancy sites (defects) therein.

The dealuminated framework was then contacted with a reflux agent and a tin precursor and heated under reflux conditions in an argon atmosphere to produce the stannosilicates. Reflux agents used included isopropanol (IPA; $C_3H_8O$) and dichloromethane (DCM; $CH_2Cl_2$). In a typical procedure using IPA, a dealuminated zeolite sample was dried in a flask under vacuum conditions (about 0.005 kPa) and, separately, isopropanol was dried using molecular sieves in an inert atmosphere (argon). Solutions of tin (IV) chloride (0.027-0.081 mol Sn (g zeolite)$^{-1}$) were prepared by adding tin (IV) chloride pentahydrate ($SnCl_4 \cdot 5H_2O$) with dry isopropanol. Then, dry isopropanol (100 $cm^3$ (g zeolite)$^{-1}$) and the tin (IV) chloride solution were added to the flask containing the zeolite sample and heated to a temperature of 383 K for seven hours under reflux conditions in argon. For the DCM procedure, dichloromethane was dried using molecular sieves in argon prior to grafting procedures. The dichloromethane was added to a flask containing a dealuminated zeolite sample and then a Sn precursor ($SnCl_4$ (1 M) in dichloromethane) was added (0.001-0.040 mol Sn (g zeolite)$^{-1}$). Then, the solution was heated to 333 K for seven hours under reflux conditions in argon.

The synthetic protocols used to prepare all Sn-Beta samples, together with their elemental composition and fraction of vacancies grafted by Sn, are listed in Table 1. Each sample is denoted as M-Beta-X-Y, where M represents the heteroatom in the framework, X represents the mineralizing agent used to synthesize the parent Al-Beta zeolite (OH— or F—), and Y reflects the Si/M ratio measured by atomic absorption spectroscopy (AAS) in the final Beta zeolites. Various techniques were performed to characterize the resulting stannosilicates.

TABLE 1

| Catalyst | Solvent | Sn concentration in reflux solution ($10^{-3}$ mol Sn $(g_{zeolite})^{-1}$) | Initial Si/Al ratio of parent Al-Beta zeolite | Si/Sn (Sn wt. %) (errors in Sn wt. % are ±15%) | Sn/vacancy (errors are ±21%) |
|---|---|---|---|---|---|
| Sn-Beta-OH-95 | DCM | 1 | 19 | 95 (2.0) | 0.20 |
| Sn-Beta-OH-46 | DCM | 10 | 19 | 46 (4.1) | 0.41 |
| Sn-Beta-OH-41 | DCM | 27 | 19 | 41 (4.6) | 0.46 |
| Sn-Beta-OH-30 | DCM | 40 | 19 | 30 (6.1) | 0.64 |
| Sn-Beta-OH-80 | DCM | 1 | 29 | 80 (2.4) | 0.36 |
| Sn-Beta-OH-40 | DCM | 10 | 29 | 40 (4.7) | 0.73 |
| Sn-Beta-OH-32 | DCM | 27 | 29 | 32 (5.8) | 0.90 |
| Sn-Beta-OH-84 | DCM | 1 | 54 | 84 (2.3) | 0.64 |
| Sn-Beta-OH-47 | DCM | 10 | 54 | 47 (4.0) | 1.15 |
| Sn-Beta-OH-144 | DCM | 0.5 | 22 | 144 (1.4) | 0.15 |
| Sn-Beta-OH-457 | IPA | 27 | 15 | 457 (0.4) | 0.03 |
| Sn-Beta-OH-200 | IPA | 81 | 54 | 200 (1.0) | 0.27 |
| Sn-Beta-OH-170 | IPA | 27 | 25 | 170 (1.2) | 0.13 |

Previous studies of isopropanol-assisted Sn grafting have concluded that Sn can incorporate within only a subset of available framework vacancies (e.g., Sn/vacancy=0.11, Si/Sn=121), beyond which additional Sn incorporation forms extraframework $SnO_2$ domains that lead to increases in the intensity of diffuse reflectance UV-visible (DRUV) bands centered at about 255 nm. At first glance, the higher fraction of framework vacancies grafted here (Sn/vacancy=0.27) than typically reported (Sn/vacancy=0.11) via isopropanol-assisted reflux, together with higher fractions of vacancies grafted via reflux with anhydrous $SnCl_4$ (Sn/vacancy=0.34) and via solid-state ion exchange (e.g., Sn/vacancy=0.74), suggested that limitations to Sn incorporation are not inherently conferred by the structure or coordination of framework vacancy defects. Yet, even the Sn-Beta-OH-200 sample (Sn/vacancy=0.27) contained nearly three times more vacant than grafted defects, suggesting that using isopropanol as the reflux solvent inhibits reactions between Sn precursors and vacancy defects during reflux procedures (383 K).

Further investigations into interactions of isopropanol with dealuminated Beta surfaces and microporous voids suggested that isopropanol can competitively adsorb with Sn precursors at framework vacancy defects at typical reflux temperatures, a nonlimiting example being at about 383 K, and limit the incorporation of framework Sn centers. In contrast, experiments performed on dealuminated Beta after saturation with dichloromethane at ambient conditions suggested that the reactions of Sn precursors with framework vacancy defects should not be inhibited during dichloromethane-assisted reflux procedures at typical reflux temperatures, a nonlimiting example being at about 333 K. As such, it was determined that IPA can competitively adsorb with Sn precursors at vacancy sites and limit the incorporation of Sn, whereas DCM did not inhibit the reaction of Sn precursors with vacancy sites.

Sn grafting via dichloromethane reflux was performed onto the same dealuminated Beta sample used to prepare Sn-Beta-OH-200, which was grafted in isopropanol, but using an about eight times lower Sn concentration (0.010 mol Sn (g zeolite)$^{-1}$) than was present during isopropanol reflux (0.081 mol Sn (g zeolite)$^{-1}$). The resulting Sn-Beta-OH-47 sample retained structural properties of the Beta topology and contained predominantly framework Sn centers. The amount of Sn grafted in Sn-Beta-OH-47 was more than four times larger than in Sn-Beta-OH-200, in spite of the about eight times lower Sn concentration present in the reflux solution with the same dealuminated Beta zeolite (initial Si/Al=54). Furthermore, the number of Sn atoms grafted into Sn-Beta-OH-47 (0.00034 mol Sn (g zeolite)$^{-1}$) was equivalent, within experimental accuracy, to the number of Al vacancies present in the dealuminated Beta support (0.0003 mol (g zeolite)$^{-1}$). These findings indicated that dichloromethane does not inhibit the reaction of Sn precursors with framework vacancy defects, as occurs in the case of isopropanol, and further that Sn grafting can occur within substantially all framework vacancies present in a given dealuminated Beta zeolite.

Figure 2:
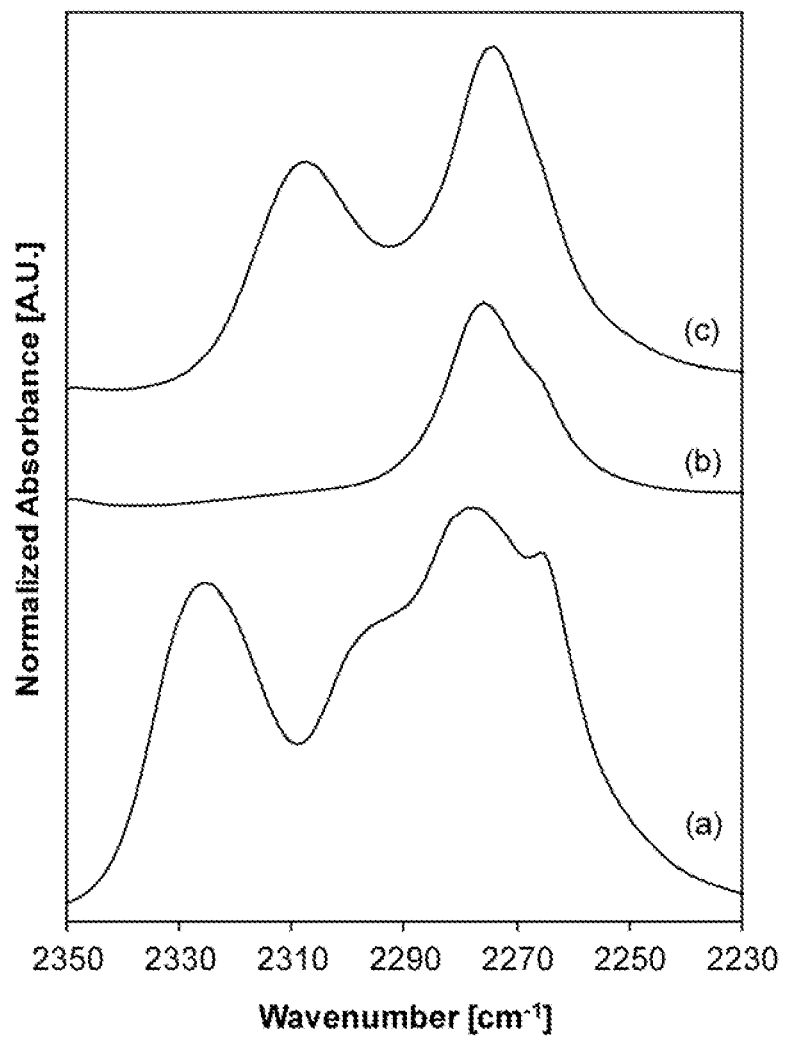
FIG. 2 includes plots of IR spectra of (a) Al-Beta-OH-54, (b) dealuminated Beta, and (c) Sn-Beta-OH-47 after saturation with $CD_3CN$ (303 K).

The incorporation of Sn centers within the framework of Sn-Beta-OH-47 was assessed using infrared (IR) spectroscopy to monitor the v(OH) and v(CN) stretching regions before and after saturation with $CD_3CN$ (303 K). IR spectra of the parent Al-Beta-OH-54, the dealuminated Beta formed via nitric acid treatment, and the final Sn-Beta-OH-47 prepared via dichloromethane-assisted reflux are shown in FIG. 1. The spectrum of Al-Beta-OH-54 shows peaks at 3610 cm$^{-1}$ for Brønsted acidic Si—OH—Al groups and at 3660 cm$^{-1}$ for perturbed Al—OH groups. These peaks disappear upon dealumination, with the concomitant appearance of peaks at 3500-3600 cm$^{-1}$ for silanol nests and at 3740 cm$^{-1}$ for isolated silanol groups. The incorporation of Sn in Sn-Beta-OH-47 causes disappearance of features in the 3500-3600 cm$^{-1}$ range and restoration of the peak at 3740 cm$^{-1}$, reflecting the preferential consumption of silanol nests during Sn grafting (FIG. 1). The spectrum of Al-Beta-OH-54 at saturation coverages with $CD_3CN$ (FIG. 2) shows peaks at 2265 cm$^{-1}$ for physisorbed $CD_3CN$, at 2275 cm$^{-1}$ for $CD_3CN$ hydrogen bound to silanol groups, at 2290 cm$^{-1}$ for $CD_3CN$ bound to Brønsted acidic Si—OH—Al groups, and at 2325 cm$^{-1}$ for $CD_3CN$ bound to Lewis acidic Al sites. The spectrum of dealuminated Beta (FIG. 2) only contains peaks for $CD_3CN$ hydrogen bound to silanol groups (2275 cm$^{-1}$) and in the gas-phase or physisorbed within microporous voids (2265 cm$^{-1}$), but not for any $CD_3CN$ at Brønsted or Lewis acid sites. The spectrum for Sn-Beta-OH-47 contains peaks at 2287 cm$^{-1}$, 2308 cm$^{-1}$, and 2316 cm$^{-1}$ that have been assigned to $CD_3CN$ bound to highly-defective Sn sites (e.g., $(SiO)_2Sn(OH)_2$), closed Sn sites, and open Sn sites in Sn-Beta, respectively (FIG. 2). Taken together, these IR spectra provided evidence for complete dealumination to form silanol nest defects, which are preferentially grafted with Sn precursors via dicholoromethane-assisted reflux to form predominantly open and closed Lewis acidic Sn sites in the framework.

The numbers of open and closed Lewis acidic Sn sites in Sn-Beta-OH-47 were quantified from integrated molar extinction coefficients for their respective IR peaks centered at 2316 cm$^{-1}$ and 2308 cm$^{-1}$, which were deconvoluted from IR spectra after CD$_3$CN saturation at 303 K according to known procedures. The numbers of open and closed Sn sites present in each sample in this investigation are summarized in Table 2. On Sn-Beta-OH-47, the number of Lewis acidic Sn sites (per mol Sn) was 0.80, within unity considering the error of the deconvolution procedure (±20%). The number of Lewis acidic Sn sites (per mol Sn) in Sn-Beta-OH-47 was also quantified from IR spectra collected after saturation with pyridine at 423 K, and from integrated molar extinction coefficients from literature. Pyridine titrated 1.15 Lewis acidic Sn sites (per mol Sn) on Sn-Beta-OH-47, also within experimental accuracy of unity (±20%), suggesting that Sn atoms are preferentially incorporated within tetrahedral framework positions and consistent with DRUV spectra collected after dehydration. These data provided quantitative evidence that Sn can be grafted indiscriminately within substantially all framework vacancies (greater than 90%) in a given dealuminated Beta zeolite via dichloromethane-assisted reflux, while avoiding the formation of extraframework SnO$_2$, providing access to routes that enable precisely controlling the framework Sn content and residual silanol defect density.

TABLE 2

| Catalyst | Lewis Acidic Sn (per total Sn) (errors are ±20%) | Open Sn Sites (per total Sn) (errors are ±20%) | Closed Sn Sites (per total Sn) (errors are ±20%) |
| --- | --- | --- | --- |
| Sn-Beta-OH-95 | 1.22 | 0.49 | 0.73 |
| Sn-Beta-OH-46 | 0.92 | 0.22 | 0.70 |
| Sn-Beta-OH-41 | 1.32 | 0.50 | 0.82 |
| Sn-Beta-OH-30 | 0.72 | 0.18 | 0.54 |
| Sn-Beta-OH-80 | 1.01 | 0.42 | 0.59 |
| Sn-Beta-OH-40 | 1.21 | 0.36 | 0.85 |
| Sn-Beta-OH-32 | 0.81 | 0.29 | 0.53 |
| Sn-Beta-OH-84 | 1.21 | 0.24 | 0.96 |
| Sn-Beta-OH-47 | 0.80 | 0.19 | 0.61 |
| Sn-Beta-OH-144 | 1.17 | 0.43 | 0.73 |
| Sn-Beta-OH-457 | 0.52 | 0.26 | 0.26 |
| Sn-Beta-OH-200 | 0.69 | 0.15 | 0.54 |
| Sn-Beta-OH-170 | 0.73 | 0.46 | 0.28 |

The ability to graft Sn atoms within virtually every silanol nest defect present in a dealuminated zeolite suggested that dichloromethane-assisted reflux procedures can be adjusted precisely to prepare Sn-Beta zeolites with a desired Si/Sn ratio, by varying the Al content in the parent zeolite or the fraction of vacancies grafted within a given dealuminated zeolite support.

Figure 3:
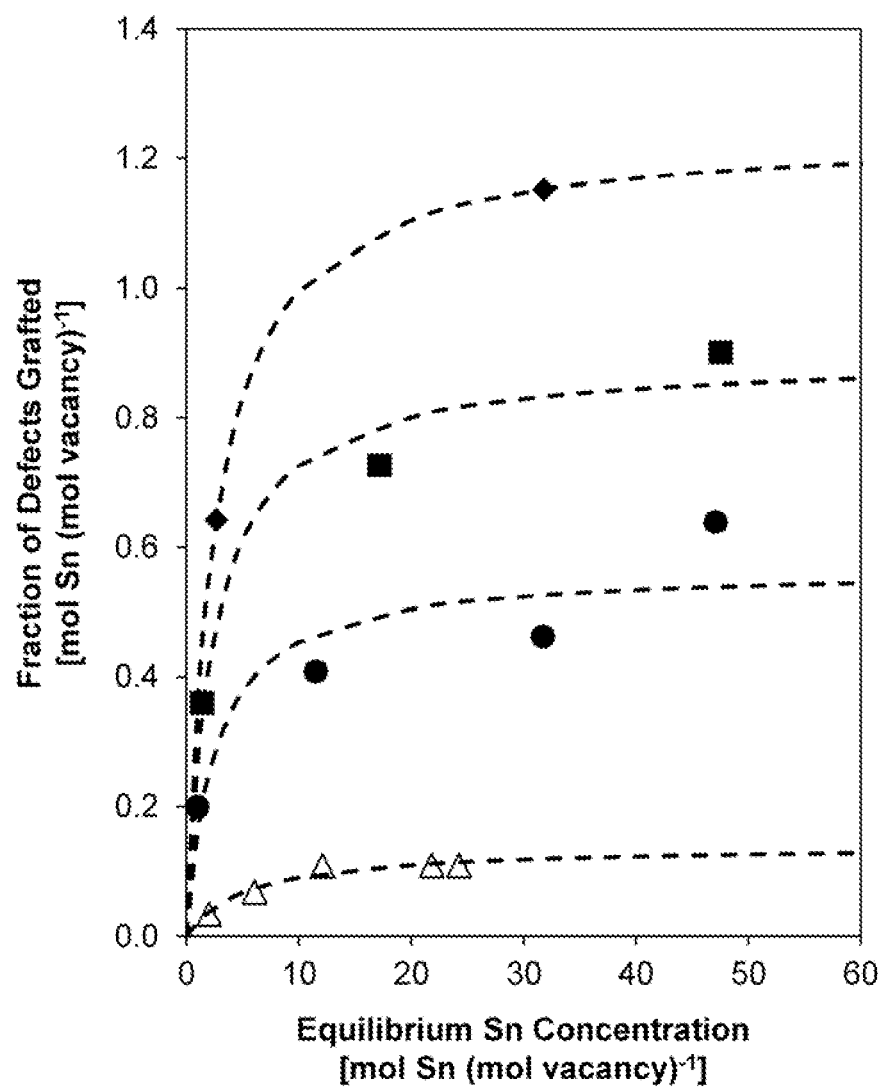
FIG. 3 is a plot representing a fraction of vacancies grafted as a function of the equilibrium Sn concentration in a reflux solution (per vacancy defects) for Sn-Beta-OH samples grafted in dichloromethane reflux from parent Al-Beta-OH-54 (solid diamond), Al-Beta-OH-29 (solid square), and Al-Beta-OH-19 (solid circle), and Sn-Beta samples grafted using isopropanol reflux reported previously (triangle). Dashed lines represent the best-fit Langmuir isotherms for each Sn-Beta-OH series.
Figure 4:
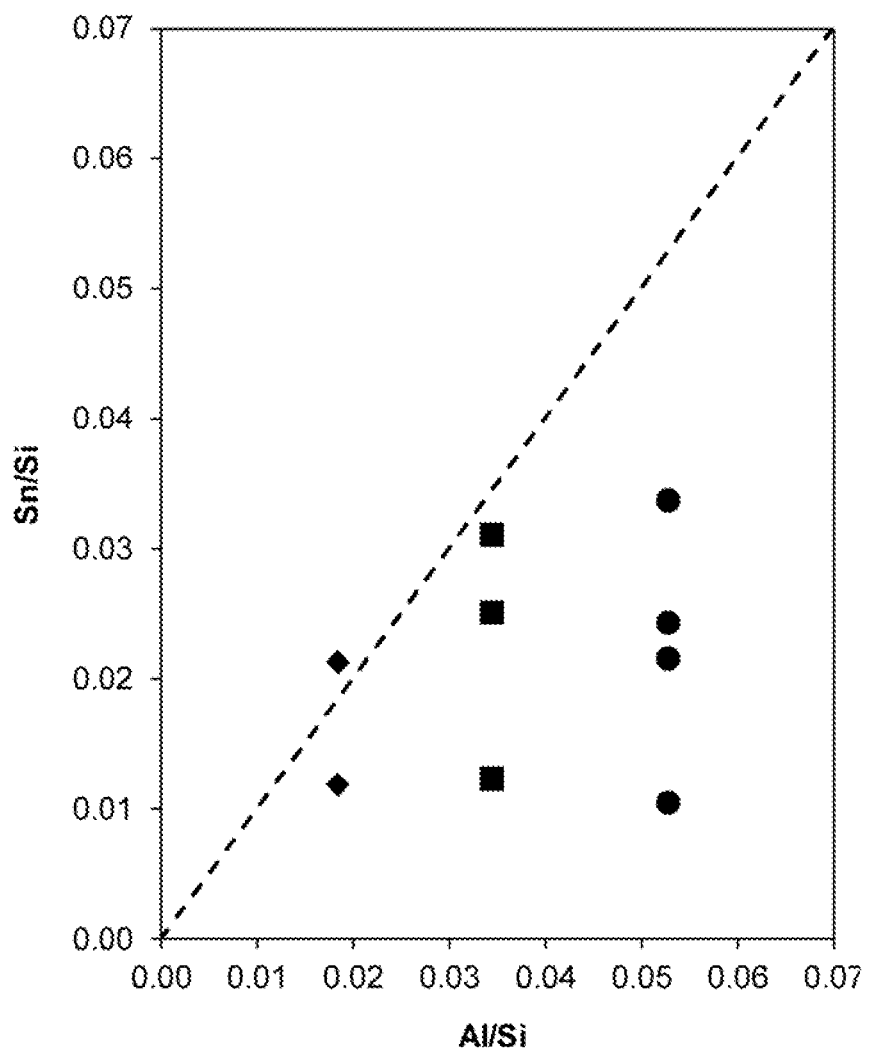
FIG. 4 is a plot representing Sn content and Al content (in the parent Al-Beta) with starting Al-Beta-OH-54 (solid diamond), Al-Beta-OH-29 (solid square), and Al-Beta-OH-19 (solid circle). The dashed line denotes the parity line.

The number of Sn atoms (per vacancy) incorporated into the final Sn-Beta-OH solids is plotted in FIG. 3 as a function of the Sn concentration in the reflux solution for samples prepared via dichloromethane grafting, together with Sn-Beta samples that contained predominantly framework Sn prepared via isopropanol grafting. Among Sn-Beta-OH samples grafted under dichloromethane reflux, Sn atoms were incorporated into framework positions at more than twice the densities when compared to samples prepared by grafting in isopropanol reflux, at the same or even at lower Sn concentrations in the reflux solution (FIG. 3), reflecting the inhibition of grafting caused by competitive adsorption of isopropanol at framework vacancy defects. The amount of Sn incorporated within each of the starting dealuminated Beta samples increased with Sn concentration in the dichloromethane reflux solution according to Langmuirian behavior and the following expression:

$$\theta_{Sn} = \frac{[Sn^*]}{[*]_0} = (\theta_{max})\frac{K[Sn]}{1 + K[Sn]} \quad \text{Eq. 1}$$

where [Sn*] is the concentration of vacancy defects incorporated with Sn atoms, [*]$_0$ is the concentration of vacancy defects present initially on the dealuminated Beta support, K is the equilibrium constant relating Sn incorporated within a vacancy defect to the Sn present in the reflux solution, [Sn] is the equilibrium Sn concentration in the reflux solution (per vacancy), and $\theta_{max}$ is the fraction of vacancies that can be grafted in a given dealuminated Beta support. The fraction of vacancies grafted ($\theta_{Sn}$) for each Sn-Beta-OH series as a function of the Sn concentration in the reflux solution (per vacancy) were regressed to Eq. (1) and plotted as dashed lines in FIG. 3, with corresponding numerical values for K and $\theta_{max}$ given in Table 3. Values of K were invariant among the three different Sn-Beta-OH series prepared via grafting in dichloromethane (333 K), yet were lower by two times for Sn-Beta-OH grafted in isopropanol (383 K), reflecting both the different temperatures used and the different Gibbs free energy differences between adsorption of Sn precursors and the solvent at vacancy defect sites. Values of $\theta_{max}$ (Table 3) were greater than five times higher for Sn-Beta-OH samples grafted using dichloromethane than those grafted using isopropanol as the reflux solvent, approaching values of one for two different dealuminated Beta supports (Table 3). Using dichloromethane-assisted reflux procedures, framework vacancies present in dealuminated Al-Beta-OH-29 and Al-Beta-OH-54 zeolites were nearly completely grafted (Sn>0.90, FIGS. 3 and 4) at sufficiently high Sn concentrations in the reflux solution, while only a fraction of those present ($\theta_{max}$=0.58, Table 3) in dealuminated Al-Beta-OH-19 zeolites were apparently able to be grafted with Sn, perhaps reflecting the higher density of vacancy defects present initially, some fraction of which may change structure after high temperature oxidative treatments so as to be incompatible hosts for Sn heteroatoms.

TABLE 3

| Parent sample | Solvent | K | $\theta_{max}$ |
| --- | --- | --- | --- |
| Al-Beta-OH-19 | DCM | 0.40 | 0.57 |
| Al-Beta-OH-29 | DCM | 0.43 | 0.89 |
| Al-Beta-OH-54 | DCM | 0.40 | 1.24 |
| Al-Beta-OH-13 | IPA | 0.18 | 0.14 |

Figure 5:
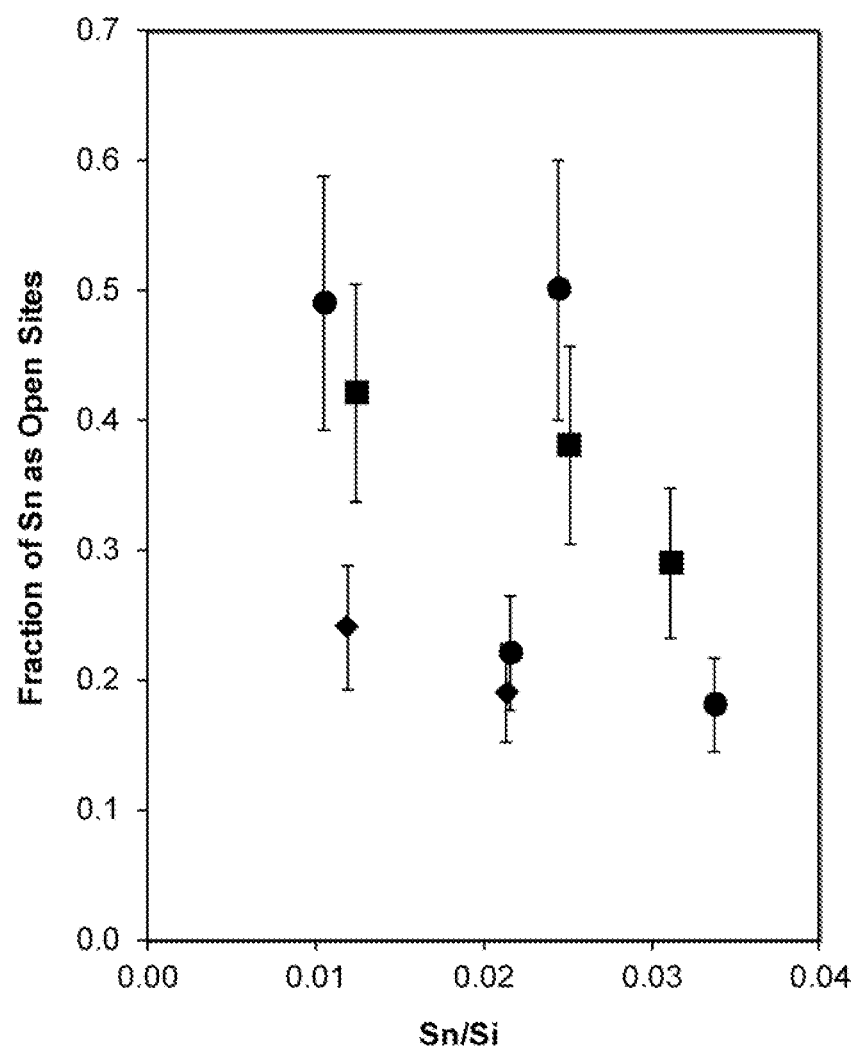
FIG. 5 includes data representing a fraction of open Sn sites as a function of bulk Sn content in Sn-Beta-OH samples grafted under dichloromethane reflux starting from Al-Beta-OH-54 (solid diamond), Al-Beta-OH-29 (solid square), and Al-Beta-OH-19 (solid circle).

The fraction of open Sn sites quantified by CD$_3$CN IR (Table 2) is plotted as a function of total Sn content in FIG. 5 for Sn-Beta-OH samples prepared via dichloromethane-assisted reflux starting from dealuminated versions of Al-Beta-OH-19, Al-Beta-OH-29, and Al-Beta-OH-54. Within each Sn-Beta-OH series, the fraction of open Sn sites decreased systematically with increasing Sn content (FIG. 5), except for Sn-Beta-OH-41, which appears to be the sole outlier among these nine samples. These site quantification data indicated that dichloromethane-assisted grafting procedures preferentially incorporates open Sn sites at low framework Sn densities. As such, the data in FIG. 5 describe one of the rare instances in which the open-to-closed Sn site ratio can be systematically varied using a given synthesis or treatment procedure. Systematic changes in open and closed Sn site fractions with Sn content will, in turn, cause systematic turnover rate dependancies for catalytic reactions that preferentially turnover on one of the two sites.

Glucose-to-fructose isomerization proceeds via quasi-equilibrated adsorption and ring opening of glucose onto an open Sn site, kinetically-relevant intramolecular 1,2-hydride shift, and quasi-equilibrated ring closing and desorption of fructose. Aqueous-phase isomerization turnover rates (per open Sn, 373 K) on Sn-Beta-OH samples are first-order in glucose concentration under dilute conditions (1-10% (w/w) glucose), in which two water molecules coordinated at Sn sites are most abundant surface intermediates. These mechanistic assumptions result in a glucose-to-fructose isomerization rate expression given by:

$$r_{isom} = \alpha \frac{K_1 k_2}{K_4 K_5} C_G = k_{isom} C_G \qquad \text{Eq. 2}$$

where α represents a product of activity coefficients of reactants and intermediate species, $k_2$ is the intrinsic rate constant for intramolecular 1,2-hydride shift, $K_1$ is the equilibrium constant for glucose adsorption from the aqueous phase to ring-opened glucose intermediates at Sn sites, $K_4$ and $K_5$ are equilibrium constants for the sequential adsorption of two water molecules at Sn sites, $C_G$ is the glucose concentration in water, and $k_{isom}$ is the measured first-order isomerization rate constant.

Figure 6:
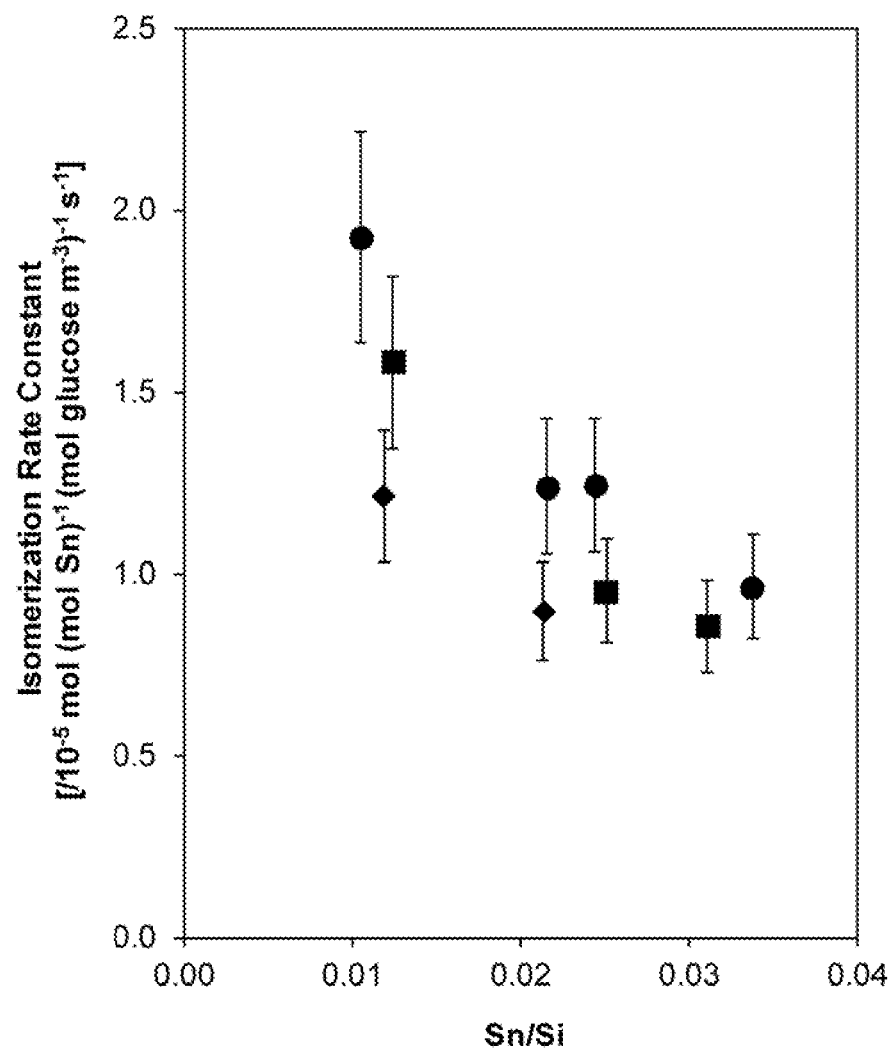
FIG. 6 includes data representing glucose isomerization rate constants (per total Sn, 373 K) and the Sn contents in Sn-Beta-OH samples grafted using dichloromethane as the reflux solvent starting from Al-Beta-OH-54 (solid diamond), Al-Beta-OH-29 (solid square), and Al-Beta-OH-19 (solid circle).

The glucose conversions, turnover numbers, and monosaccharide yields in the batch reactor experiments used to measure kinetic data on each Sn-Beta sample are shown in Table 4, confirming both their differential and catalytic nature. Measured first-order isomerization rate constants (373 K), normalized by the total number of Sn sites, are shown in FIG. 6 for Sn-Beta-OH samples grafted using dichloromethane as the reflux solvent. Rate constants (per total Sn, 373 K) varied by about 2.5 times among samples of widely varying Sn content (Si/Sn=30-95), and decreased systematically with increasing Sn content within each Sn-Beta-OH series, as observed previously for Sn-Beta samples prepared via post-synthetic grafting using isopropanol and via solid-state ion exchange. Decreases in isomerization rates (per total Sn, 383 K) with increasing Sn content have been previously ascribed to intracrystalline mass transfer limitations, yet the isomerization rates reported in FIG. 6 are uncorrupted by transport limitations, reflected in the kinetic isotope effect value of about 2.1 (at 373 K) measured when using glucose reactants deuterated at their α-carbonyl position. Decreases in glucose isomerization rates (per total Sn, 383 K) with increasing Sn content have also been speculated to reflect differences in Sn siting at different T-site locations. The $CD_3CN$ titration data shown in FIG. 5, however, indicated that the fraction of open Sn sites decreases systematically with increasing Sn content within each series of Sn-Beta-OH samples.

TABLE 4

| Catalyst | Conversion (%) | Monosaccharide Yield (w/w %) | | | Total moles of product per mole of open Sn sites | $k_{isom}$ (per open Sn)* (errors are ±15%) |
| --- | --- | --- | --- | --- | --- | --- |
| | | Glucose | Fructose | Mannose | | |
| Sn-Beta-OH-95 | 4.5 | 96 | 4 | not detected | 2.5 | 3.9 |
| Sn-Beta-OH-46 | 5.2 | 94 | 5 | 0.3 | 3.8 | 5.6 |
| Sn-Beta-OH-41 | 5.9 | 93 | 6 | 0.3 | 1.7 | 2.5 |
| Sn-Beta-OH-30 | 6.1 | 93 | 6 | 1 | 4.1 | 5.4 |
| Sn-Beta-OH-80 | 4.6 | 95 | 5 | not detected | 2.4 | 3.8 |
| Sn-Beta-OH-40 | 3.2 | 97 | 3 | not detected | 1.2 | 2.5 |
| Sn-Beta-OH-32 | 3.4 | 97 | 3 | not detected | 1.4 | 3.0 |
| Sn-Beta-OH-84 | 2.0 | 98 | 2 | not detected | 2.4 | 5.1 |
| Sn-Beta-OH-47 | 2.6 | 97 | 3 | not detected | 2.3 | 4.7 |
| Sn-Beta-OH-144 | 1.8 | 98 | 2 | not detected | 2.1 | 4.3 |
| Sn-Beta-F-93 | 5.3 | 94 | 5 | 1 | 3.3 | 5.7 |
| Sn-Beta-F-50 | 6.0 | 93 | 6 | 1 | 2.9 | 4.9 |
| Sn-Beta-OH-457 | 2.1 | 98 | 2 | not detected | 11.0 | 1.4 |
| Sn-Beta-OH-200 | 2.4 | 98 | 2 | not detected | 4.5 | 1.5 |
| Sn-Beta-OH-170 | 3.1 | 97 | 3 | not detected | 7.9 | 0.8 |

*Units are $10^{-5}$ mol (mol open Sn)$^{-1}$ (mol glucose m$^{-3}$)$^{-1}$ s$^{-1}$.

Figure 7:
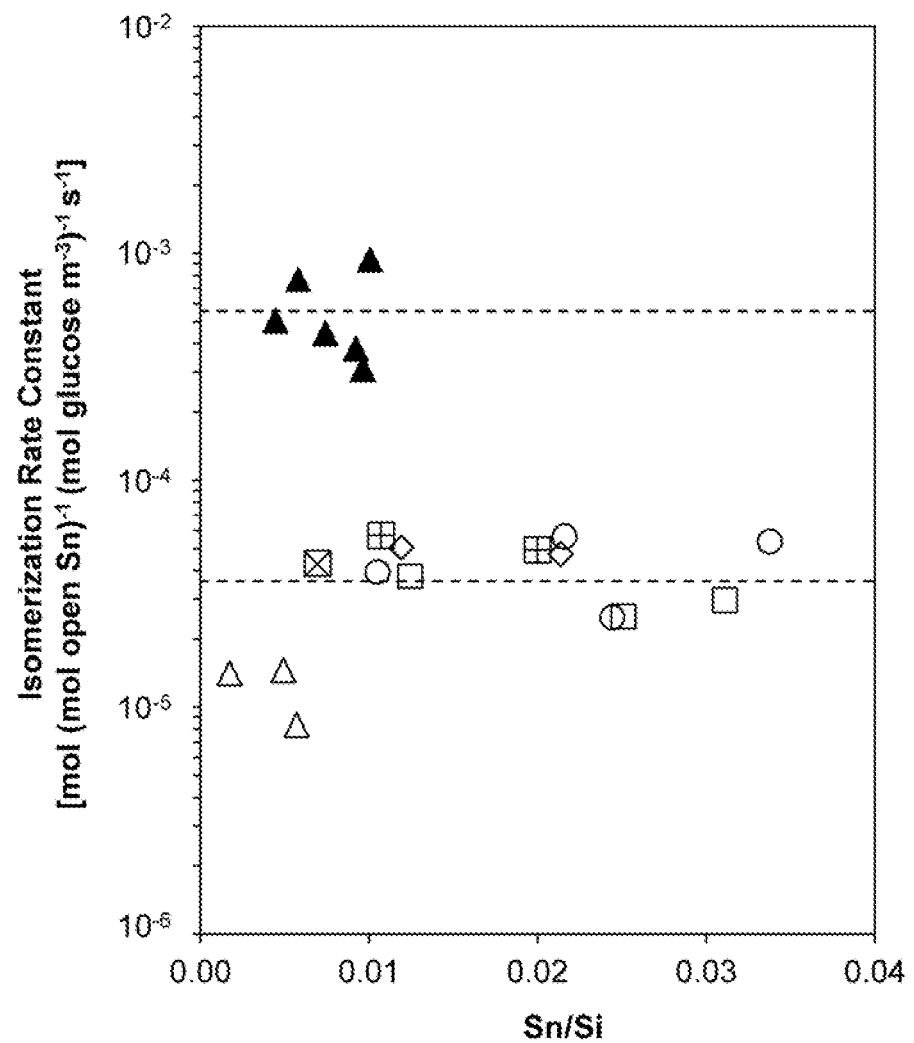
FIG. 7 is a plot representing isomerization rate constants (per open Sn, 373 K) and Sn contents for Sn-Beta-OH samples grafted in isopropanol reflux (triangle), in dichloromethane reflux starting from Al-Beta-OH-54 (diamond), Al-Beta-F-45 (four square grid), Al-Beta-OH-29 (square), Al-Beta-OH-22 (square with an x), Al-Beta-OH-19 (circle), and hydrothermally-synthesized Sn-Beta-F (solid triangle). Dashed lines represent the average rate constant (per open Sn, 373 K) for Sn-Beta-F samples prepared hydrothermally and Sn-Beta-OH samples.

First-order isomerization rate constants (373 K), normalized by the number of open Sn sites (Table 2), for all post-synthetically prepared Sn-Beta samples are given in Table 4 and are plotted in FIG. 7 as a function of Sn content, together with rate constants on hydrothermally-synthesized Sn-Beta samples reported previously. Among the different Sn-Beta-OH samples prepared by dichloromethane-assisted reflux, isomerization rate constants (per open Sn, 373 K) are similar (within about two times) and do not depend systematically on Sn content, which is the single-site kinetic behavior expected upon accurate normalization of turnover rates by the number of reactive Sn sites. Interestingly, values of $k_{isom}$ (per open Sn, 373 K, FIG. 7) were consistently about three times higher among Sn-Beta-OH samples prepared via grafting in dichloromethane reflux than those in isopropanol reflux. The underlying reasons for the rate constant differences among these two sample sets remain unclear, although unlikely to reflect differences in framework Sn site distribution considering that Sn-Beta-OH-170 and Sn-Beta-OH-144 samples respectively grafted in isopropanol and dichloromethane contain similar framework Sn and residual vacancy content (Table 1). The small variations in $k_{isom}$ values (within about two times, 373 K) among the ten post-synthetic Sn-Beta-OH samples prepared via dichloromethane reflux (FIG. 7) can be accounted for by differences of only 2.5 kJ mol$^{-1}$ in apparent Gibbs free energies of activation, and resemble the similar variation (within about three times, 373 K) reported previously among six hydrothermally-synthesized Sn-Beta-F samples (FIG. 7). It was concluded that isomerization rates (per total Sn) among post-synthetically prepared Sn-Beta zeolites decrease systematically with increasing Sn content (FIG. 6) because open Sn sites are the dominant active site for glucose-to-fructose isomerization and are incorporated preferentially at low Sn content when Sn-Beta samples are prepared via grafting procedures (FIG. 5).

In contrast to the small variations (about 3-5 times) in $k_{isom}$ values among post-synthetically prepared, high-defect Sn-Beta-OH zeolites, higher $k_{isom}$ values (by about 15-50 times) were measured on hydrothermally-synthesized, low-defect Sn-Beta-F samples (FIG. 7), as reported previously. Such kinetic behavior suggests that Gibbs free energy differences between intramolecular 1,2-hydride shift transition states and two coordinated water ligands, which are the most abundant surface intermediates on open Sn sites under these reaction conditions, are larger in the presence of co-adsorbed hydrogen-bonded water networks that exist within high-defect Sn-Beta-OH zeolite pores, but not within low-defect Sn-Beta-F pores, during conditions of aqueous-phase catalysis (373 K). The similar $k_{isom}$ values (per open Sn, 373 K) among the ten Sn-Beta-OH samples grafted in dichloromethane, which contain a wide range of residual vacancy defect densities (Sn/vacancy=0.15-1.15), indicated that glucose isomerization turnover rates in this kinetic regime are insensitive to the residual silanol density. It was speculated that this insensitivity reflects a critical density of hydrophilic binding sites, including both Sn heteroatoms and silanol defects (of at most $3 \times 10^{-4}$ mol (g zeolite)$^{-1}$) required to stabilize hydrogen-bonded water networks throughout zeolitic micropores during conditions of aqueous-phase catalysis (373 K).

Therefore, it was hypothesized that preparing an Al-Beta zeolite in fluoride media, which should form low-defect frameworks containing predominantly hydrophobic siloxane (Si—O—Si) connectivities, could be subject to dealumination treatments and subsequent dichloromethane-assisted grafting of tin precursors in order to prepare a post-synthetic Sn-Beta-F sample with low residual defect density. Sn-Beta-F-93 and Sn-Beta-F-50 samples were prepared in this manner and indeed showed H$_2$O uptakes (P/P$_0$=0.2 at 293 K, used elsewhere as a descriptor of hydrophobicity) that were about 3.5 times lower than the H$_2$O uptakes averaged among the Sn-Beta-OH sample series. When normalized on a total Sn basis, the first-order glucose isomerization rate constant (373 K) on Sn-Beta-F-93 was about three times larger than for the Sn-Beta-OH samples and only about 3.5 times lower than for the hydrothermally-synthesized Sn-Beta-F samples, similar to previous observations reported for Sn-Beta-F samples prepared via solid-state ion exchange of Sn onto dealuminated Beta-F supports. Surprisingly, CD$_3$CN IR spectra of Sn-Beta-F-93 at saturation coverages showed the highest fraction of Lewis acidic Sn present in open configuration (0.62, Table 5) that it was observed among more than twenty samples prepared hydrothermally or by post-synthetic grafting under isopropanol and dichloromethane reflux (Table 2). The underlying reasons why this sample showed an unprecedentedly high open-to-closed Sn site ratio (about 1.2) remains under investigation, but another Sn-Beta-F sample prepared from the same support with higher Sn content (Sn-Beta-F-50) also showed a high open-to-closed Sn site ratio (about one; Table 5). The Sn-Beta-F-50 sample also showed a smaller fraction of open sites than on Sn-Beta-F-93, consistent with the dependence of open-to-closed Sn ratio on bulk Sn content observed for the Sn-Beta-OH series (FIG. 5). First-order glucose isomerization rate constants (373 K), when normalized to the number of open Sn sites, were identical on the post-synthetically prepared Sn-Beta-F samples and on the post-synthetically prepared Sn-Beta-OH samples (FIG. 7), in spite of the H$_2$O uptake (P/P$_0$=0.2, 293 K) on Sn-Beta-F-93 that more closely resembled that of hydrothermally-synthesized Sn-Beta-F samples. These catalytic data suggest that the intrapore environments in post-synthetically prepared Sn-Beta-F samples, within which framework Sn sites are sequestered and glucose isomerization reaction coordinates are confined, resemble structurally those in post-synthetically prepared Sn-Beta-OH samples rather than hydrothermally-synthesized Sn-Beta-F samples.

Figure 8:
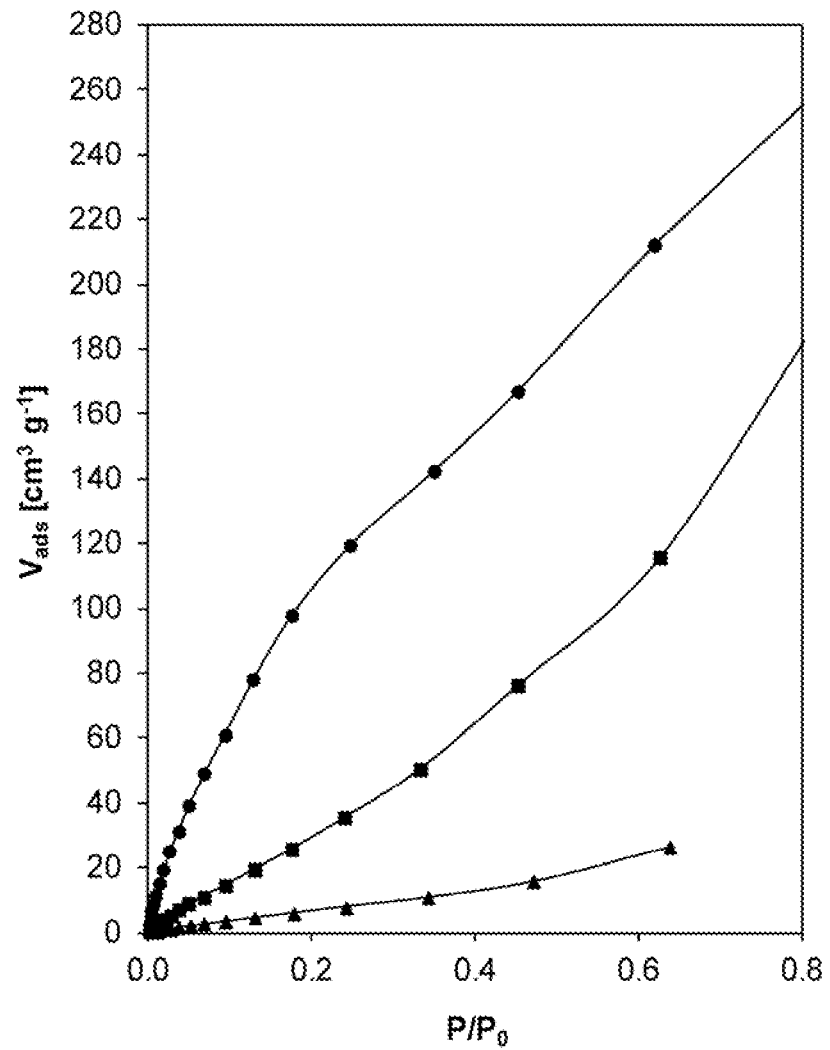
FIG. 8 is a plot representing vapor-phase $H_2O$ adsorption isotherms (293 K) of Sn-Beta-OH-80 (solid circle), Sn-Beta-F-93 (solid square), and Sn-Beta-F-220 prepared hydrothermally (solid triangle).
Figure 9:
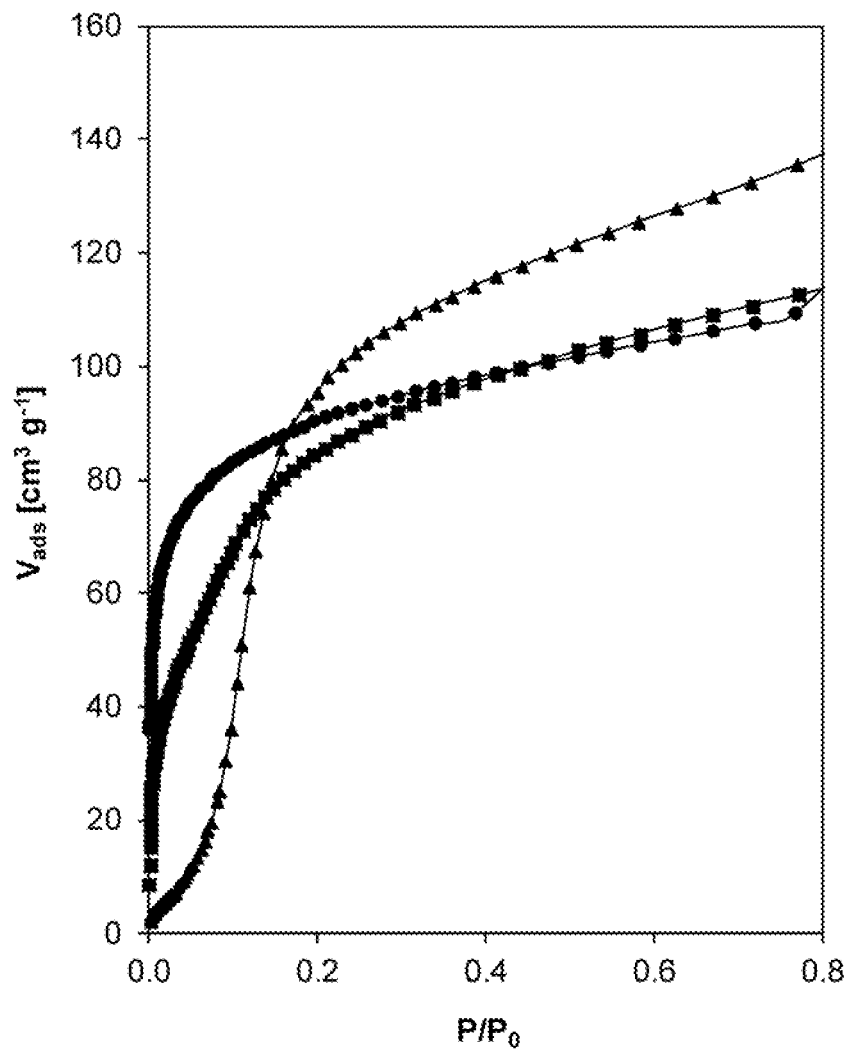
FIG. 9 is a plot representing vapor-phase $CH_3OH$ adsorption isotherms (293 K) of Sn-Beta-OH-80 (solid circle), Sn-Beta-F-93 (solid square), and Sn-Beta-F-220 prepared hydrothermally (solid triangle).

Water uptakes (P/P$_0$=0.2, 293 K) have been used previously as a proxy to describe the hydrophobic character of zeolites, given the ability of organic molecules to fill hydrophobic micropores at equivalent reduced pressures, yet such uptakes represent an integral measurement of adsorption at heteroatom sites, silanol defects within pores and at external crystal surfaces, and any other hydrophilic binding sites that may be present. In contrast, alcohols adsorb preferentially within low-defect, organophilic micropores until condensation occurs and before adsorption begins within mesopores or at external crystallite surfaces, providing a means to distinguish hydrophilic sites located within micropores and at external surfaces. H$_2$O and CH$_3$OH adsorption isotherms (293 K) measured on Sn-Beta-F-93, Sn-Beta-OH-80 (chosen as a representative Sn-Beta-OH sample), and a Sn-Beta-F sample prepared hydrothermally are shown in FIGS. 8 and 9. For the Sn-Beta-F-93 sample, the H$_2$O adsorption isotherm (FIG. 8) more closely resembled that of the hydrothermally-synthesized Sn-Beta-F sample, as reported for Sn-Beta-F samples prepared post-synthetically by solid-state ion exchange. In contrast, the CH$_3$OH adsorption isotherm (293 K) on Sn-Beta-F-93 resembled a type I isotherm (FIG. 9), reflecting micropore condensation driven by adsorbate-adsorbent interactions as observed on high-defect micropores such as those present in Sn-Beta-OH-80. These CH$_3$OH adsorption isotherms (293 K) were distinctly different than the type V adsorption isotherm measured on the low-defect hydrothermally-synthesized Sn-Beta-F sample (FIG. 9), reflecting micropore condensation driven by strong adsorbate-adsorbate interactions. As a result, the similar $k_{isom}$ values (per open Sn, 373 K) for the two post-synthetically grafted Sn-Beta-F samples (Sn-Beta-F-93, Sn-Beta-F-50) and the ten post-synthetically grafted Sn-Beta-OH samples via dichloromethane-assisted reflux appear to reflect similarities in the residual silanol defect density within their microporous voids and the kinetic consequences of such defect groups and the hydrogen-bonded water networks they stabilize during catalysis in liquid water. This interpretation suggests that subsequent treatments to further decrease the density of internal defects may increase glucose-fructose isomerization rate constants for Sn-Beta samples prepared via post-synthetic routes.

Figure 10:
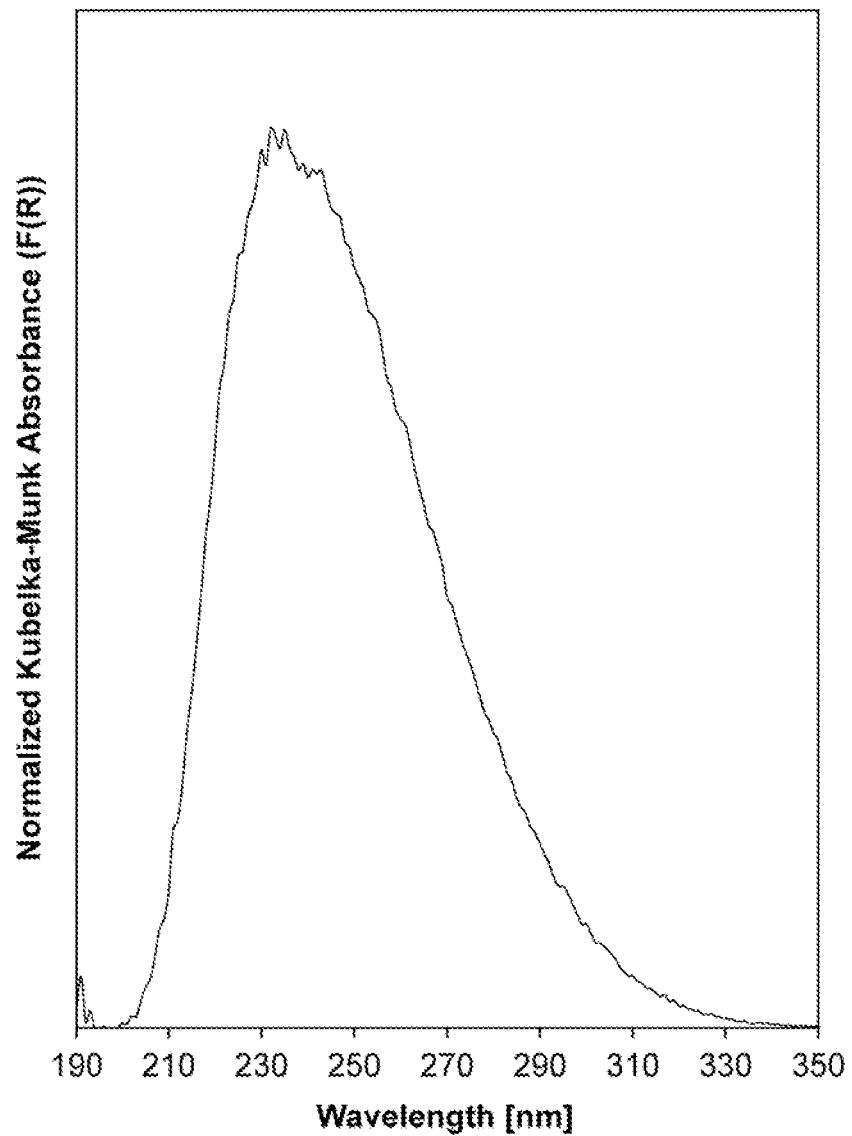
FIG. 10 is a plot representing a diffuse reflectance UV-visible (DRUV) spectrum of Ti-Beta-OH prepared via dichloromethane-assisted grafting after heat treatment at 523 K.
Figure 11:
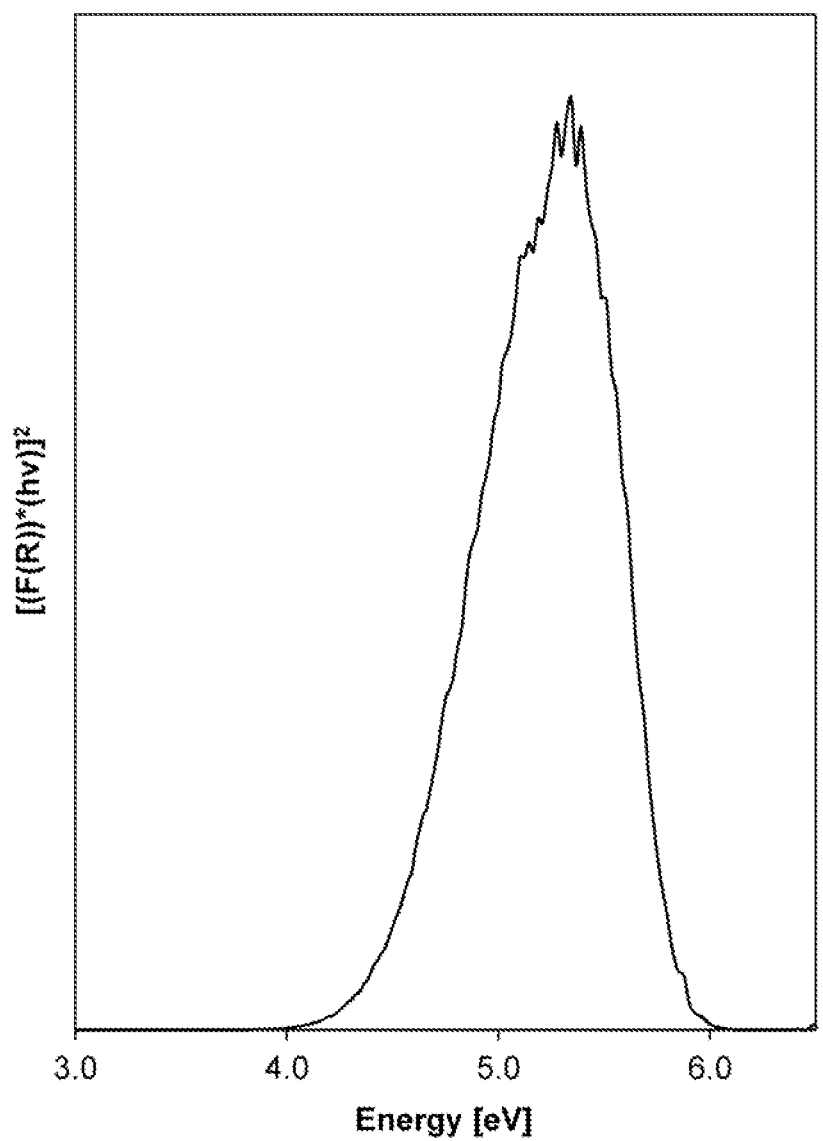
FIG. 11 is a Tauc plot of Ti-Beta-OH prepared via dichloromethane-assisted grafting after heat treatment at 523 K; edge energy=4.5 eV.
Figure 12:
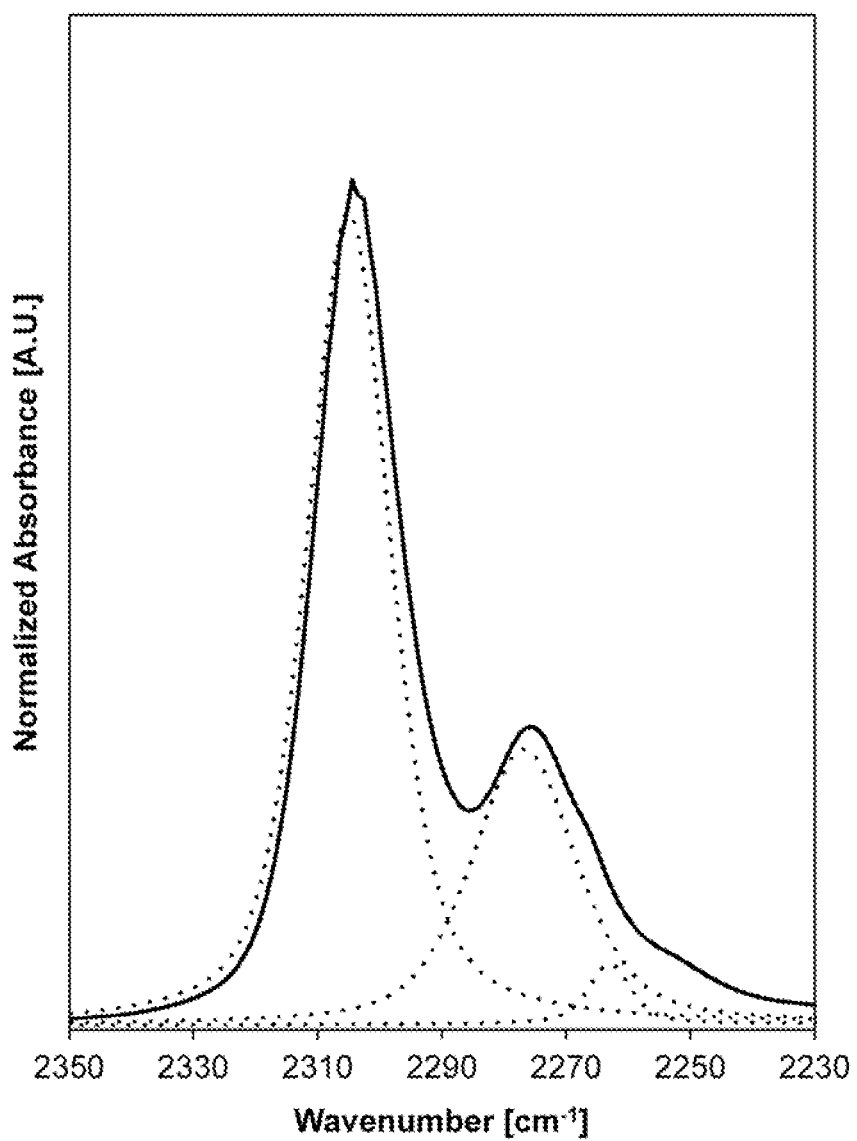
FIG. 12 is a plot representing IR spectrum of Ti-Beta-OH (solid line) after saturation with $CD_3CN$ and its deconvolution components (dashed lines) at 2265 $cm^{-1}$, 2275 $cm^{-1}$, and 2308 $cm^{-1}$ for $CD_3CN$ in the gas-phase or physisorbed, bound to silanol groups, and Lewis acidic Ti sites, respectively.

The following describes investigations that demonstrate the ability to produce zeotype materials having Ti heteroatoms incorporated into a zeolite-type framework thereof (referred to as titanosilicates). Ti-Beta zeolites were synthesized post-synthetically under dichloromethane reflux using procedures similar to those noted-above for the synthesis of stannosilicates. Multiple samples with varied Si/Ti molar ratios ranging from 34 to 297 (up to 2.3 Ti wt. %) were prepared by varying the concentration of the Ti precursor ($TiCl_4$ (1 M) in dichloromethane) in the reflux solution. As a nonlimiting example, Ti-Beta zeolites were synthesized with a Si/Ti atomic ratio of 46 (1.7 Ti wt. %) and characterized. FIGS. 10-12 represents characterization data that evidences Ti incorporation into zeolite framework vacancy positions. FIG. 10 includes a plot representing a DRUV spectrum of a Ti-Beta sample after a dehydration treatment (523 K) and shows absorption characteristic of isolated Ti centers in zeolite frameworks. FIG. 11 is a Tauc plot, prepared from DRUV spectrum of the Ti-Beta sample after dehydration (523 K), was used to calculate the edge energy (4.5 eV), which is characteristic of isolated Ti centers in zeolite frameworks. FIG. 12 includes a $CD_3CN$ infrared (IR) spectrum of a Ti-Beta sample that was used to quantify the number of Lewis acidic (i.e., framework) Ti sites, and counted a number equal to the total bulk Ti content, indicating that all Ti atoms are grafted into framework positions.

Similar to Sn heteroatoms, it is believed that Ti heteroatoms form open and closed configurations when incorporated into heteroatom sites in a zeolite-type framework. Although investigations are still ongoing, it is also believed at this time that the orientation of Ti heteroatoms may be controlled in a manner similar to the methods discussed above regarding Sn heteroatoms. This belief is based on the fact that Lewis acid metal sites in zeolite frameworks catalyze the isomerization of glucose to fructose via intramolecular 1,2-hydride shift steps. Quantum chemical calculations (e.g., density functional theory) has shown that the activation barriers for these hydride shift steps are about 20-40 kJ $mol^{-1}$ lower on metal sites of open configuration, than on metal sites of closed configuration. As a result, glucose isomerization turnover rates are higher on open sites than on closed sites, consistent with poisoning experiments using ammonia and pyridine titrants that adsorb selectively on open Sn sites and suppress glucose isomerization rates.

As seen in FIG. 6, glucose isomerization rates (normalized on a total Sn atom basis) decrease systematically with increasing total Sn content, for different series of Sn-Beta-OH samples that are prepared by post-synthetic grafting methods described herein (i.e., dichloromethane-assisted reflux of $SnCl_4$). As seen in FIG. 5, the fraction of Sn sites that are grafted in open configuration also decreases systematically with increasing total Sn content for each series of Sn-Beta-OH materials. Therefore, as seen in FIG. 7, glucose isomerization turnover rates (normalized per open Sn atom) are constant for each series of Sn-Beta-OH materials, because open Sn sites are the dominant active sites for glucose isomerization.

Figure 13:
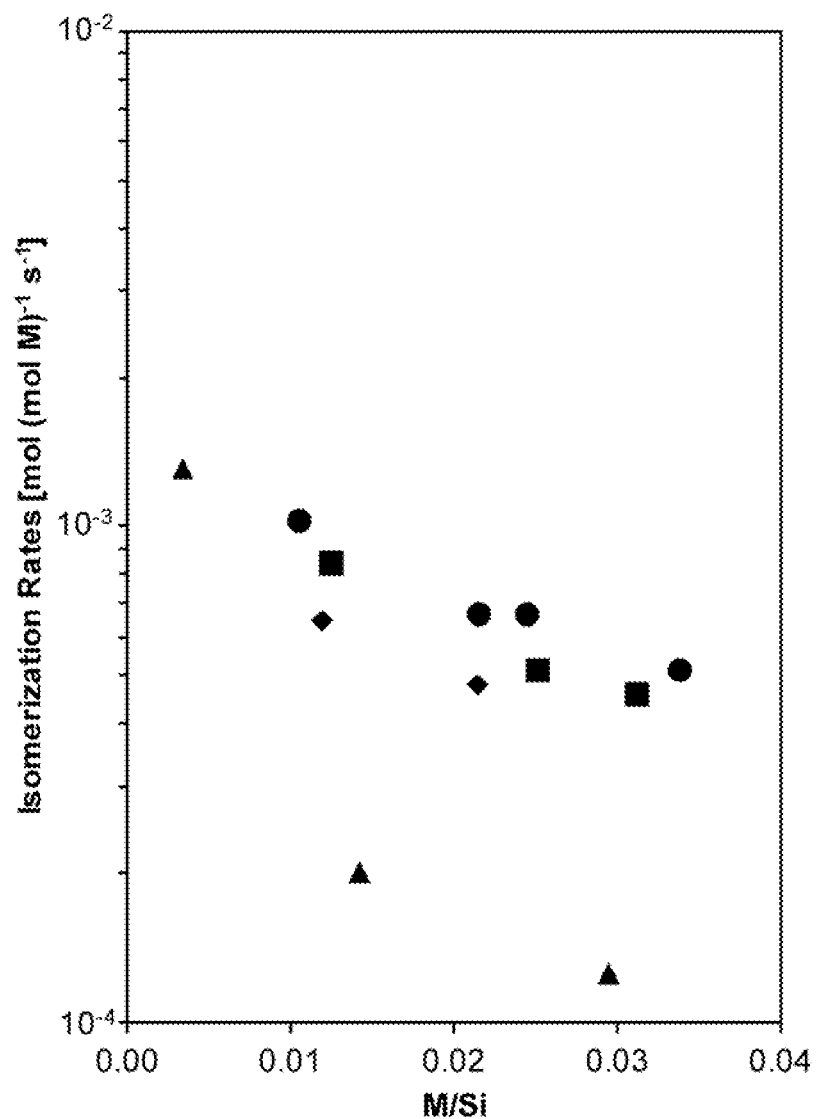
FIG. 13 is a plot that includes data representing glucose isomerization rates (per total Sn, 373 K) and the Sn contents in Sn-Beta-OH samples grafted using dichloromethane as the reflux solvent starting from Al-Beta-OH-54 (solid diamond), Al-Beta-OH-29 (solid square), and Al-Beta-OH-19 (solid circle). Additionally, FIG. 13 includes data representing glucose isomerization rates (per total Ti, 373 K) and the Ti contents in Ti-Beta-OH samples (solid triangle) grafted using dichloromethane as the reflux solvent on a dealuminated Beta zeolite.

As seen in FIG. 13, there is also an observed decrease in glucose isomerization rates (normalized on a total Ti atom basis) with increasing Ti content, among post-synthetically prepared Ti-Beta-OH zeolites using an analogous grafting method (dichloromethane-assisted grafting of $TiCl_4$ precursors).

In view of the above, and the analogous behavior observed for Sn-Beta zeolites, it is reasonable to conclude that Ti sites are preferentially grafted in open configurations at low Ti densities. In other words, it is reasonable to conclude that the relative ratio of open and closed metal sites grafted with increasing metal atom density is analogous for Sn and Ti, using the preparation methods described herein.

Therefore, it is believed that a desired Si-to-Ti atom ratio of the zeotype material and relative amounts of Ti heteroatom sites having open and closed configurations in the zeotype material can be controlled by controlling a fraction of the vacancy sites to which the Ti heteroatoms are incorporated into during the reflux step. In addition, the Ti heteroatom content in the zeotype material may be controlled in order to improve a rate of isomerization of glucose-to-fructose in the presence of the zeotype material. The density of residual vacancy defects may be controlled by synthesizing the zeolite in a fluoride media to decrease the density of the vacancy sites in the zeotype material.

Based on the investigations leading to the present invention, protocols for the selective grafting of stannic precursors within virtually every framework vacancy defect present in dealuminated Beta zeolites were developed using dichloromethane reflux (333 K), which avoids the competitive adsorption of isopropanol, a commonly used reflux solvent (383 K), at vacancy defects that inhibits the incorporation of Sn precursors. Dichloromethane-assisted reflux allows preferential grafting of Lewis acidic Sn sites in framework locations at Sn densities higher (Si/Sn=30, 6.1 wt. % Sn) than accessible via isopropanol-assisted reflux (Si/Sn greater than 120, less than 1.6 wt. % Sn). Additionally, the fraction of open Sn sites decreased systematically with increasing Sn content among Sn-Beta samples prepared via dichloromethane-assisted reflux, indicating that open Sn sites are preferentially grafted at low framework Sn densities. The ability to incorporate Sn atoms within nearly all vacancies (Sn/vacancy greater than 0.9) present in different dealuminated Beta supports demonstrates that Sn grafting can occur indiscriminately within all silanol nests and not only at a subset of vacancies with special coordination or geometry conferred by T-site location. By extension, methods to graft Sn precursors within each available framework vacancy open routes to prepare stannosilicates with tailored framework Sn site distribution among different intrazeolite locations and T-sites by controlling the placement of Al atoms in the parent zeolite framework before dealumination. The dichloromethane-assisted reflux methods to prepare Sn-Beta reported herein enable tailoring the ratio of open-to-closed framework Sn sites more systematically than hydrothermal synthesis methods, and controlling the densities of framework Sn and residual vacancy defects, by varying the initial Si/Al ratio of the parent zeolite and the Sn concentrations present in the reflux solutions. It is expected that these synthesis protocols can be adapted to incorporate other heteroatoms into framework vacancy defects, and for those located in zeolite topologies other than Beta. This expectation was supported by the investigations into Ti-Beta samples.

Aqueous-phase glucose-fructose isomerization rates (per total Sn, 373 K), measured in a kinetic regime that is first-order in extrazeolite glucose concentration, were consistently lower (about 15-50 times) among post-synthetically prepared Sn-Beta samples than among hydrothermally-synthesized Sn-Beta samples. The former contain high-defect micropore environments while the latter contain low-defect micropore environments, assessed from vapor-phase $CH_3OH$ adsorption behavior, providing guidance that removing residual intrapore hydrophilic defect sites in post-synthetically prepared Sn-Beta samples increases glucose isomerization turnover rates. Measured first-order isomerization rate constants (per total Sn, 373 K) decreased systematically with increasing Sn content for Sn-Beta-OH samples prepared post-synthetically via dichloromethane-assisted grafting. Similar observations have previously been attributed to intrazeolite mass transfer limitations or reactive heterogeneities among Sn sites at crystallographically unique framework locations, yet here reflect differences in the fraction of framework Sn sites present in "open" coordination $((SiO)_3Sn(OH))$, which give rise to peaks at 2316 $cm^{-1}$ in $CD_3CN$ IR spectra and are the dominant active sites for glucose isomerization. First-order isomerization rate constants (373 K), when normalized to the number of open Sn sites, were similar (within about two times) and did not vary systematically with Sn content among twelve Sn-Beta samples prepared via dichloromethane reflux. The invariance in rate constant (per open Sn, 373 K) for samples with widely varying Sn content (Si/Sn=30-457; 0.4-6.1 wt. % Sn) and residual silanol density reflect the single-site behavior of open Sn sites confined in a high-defect microporous environment, as expected when turnover rates are normalized accurately by the number of reactive centers.

As evidenced by the above-noted investigations, this disclosure provides a process that includes dealuminating a zeolite having a framework to remove aluminum atoms therefrom to produce a dealuminated framework comprising a plurality of vacancy sites. The dealuminated framework is contacted with dichloromethane and a precursor comprising heteroatoms and then heated under reflux conditions to incorporate the heteroatoms into at least some, preferably substantially all, of the plurality of vacancy sites in the dealuminated framework to produce a zeotype material having a zeolite-type framework comprising the heteroatoms.

The process may further include controlling a desired Si-to-metal atom ratio of the zeotype material and relative amounts of heteroatoms sites having open and closed configurations in the zeotype material by controlling a fraction of the vacancy sites to which the heteroatoms are incorporated into during the reflux step. The process may also further include controlling the heteroatom content in the zeotype material in order to improve a rate of isomerization of glucose to fructose in the presence of the zeotype material. The density of residual vacancy defects may be controlled by synthesizing the zeolite in a fluoride media to decrease the density of the vacancy sites in the zeotype material.

Zeotype materials having a zeolite-type framework comprising the heteroatoms as described herein are applicable to various applications, including use as adsorbents and catalysts. These materials are particularly beneficial for applications in which control of open and closed site coordination will likely affect the catalytic behavior (i.e., the diagnostic observation is that reaction rates, normalized by the total number of heteroatom sites, decrease as the overall number of heteroatom sites in the framework increases). As nonlimiting examples, Zeotype materials having Beta type frameworks and Sn heteroatoms formed by processes disclosed herein will likely be very beneficial as catalysts for reactions such as glucose-to-fructose isomerization, Baeyer-Villiger oxidation of cyclohexanone and hydrogen peroxide to caprolactone, Meerwein-Ponndorf-Verley reduction of cyclohexanone and 2-butanol to cyclohexanol, and conversion of 1,3-dihydroxyacetone to ethyl lactate in ethanol and 1,3-dihydroxyacetone to methyl lactate in methanol. Other nonlimiting reactions that are also catalyzed by Sn-Beta, for which control of open and closed site coordination may affect the catalytic behavior, include octene epoxidation to epoxyoctane, Diphenyl sulfide oxidation to diphenyl sulfoxide and diphenyl sulfone, Baeyer-Villiger oxidation of cyclohexanone to caprolactone and 2-adamantanone to 2-adamantanone lactone, intramolecular hydride shift of lactose to lactulose and glyceraldehyde to dihydroxyacetone, intramolecular carbon shift of glucose to mannose, intermolecular hydride shift of cyclohexanone to cyclohexanol, benzaldehyde to benzyl alcohol, 4-tert-butylcyclohexanone to 4-tertbutylcyclohexanol, and methyl levulinate to γ-valerolactone, Aldol condensation of dihydroxyacetone and paraformaldehyde to α-Hydroxy-γ-butyrolactone, and benzaldehyde and acetone to benzalacetone, and Diels-Alder of furan derivatives and ethylene to p-xylene derivatives.

Additional aspects and advantages of this invention will be further appreciated from the description contained in Juan Carlos Vega-Vila, James W. Harris, Rajamani Gounder, "Controlled Insertion of Tin Atoms into Zeolite Framework Vacancies and Consequences for Glucose Isomerization Catalysis," Journal of Catalysis, 344 (2016) 108-120; DOI: 10.1016 (hereinafter, Juan Carlos Vega-Vila et al.), whose contents are incorporated herein by reference.

While the invention has been described in terms of specific or particular embodiments and investigations, it is apparent that other forms could be adopted by one skilled in the art. For example, the zeolite and/or zeotype materials could differ in appearance and construction from the embodiments described herein, that is, comprise a framework of a different topology, process parameters such as temperatures and durations could be modified, and appropriate materials, including the heteroatoms, could be substituted for those noted. Accordingly, it should be understood that the invention is not limited to any embodiment described herein or illustrated in the drawings, nor is the invention necessarily limited by the description, results, and/or conclusions contained in Juan Carlos Vega-Vila et al. It should also be understood that the phraseology and terminology employed above are for the purpose of describing the disclosed embodiments and investigations, and do not necessarily serve as limitations to the scope of the invention. Therefore, the scope of the invention is to be limited only by the following claims.

The invention claimed is:
1. A process comprising:
providing an aluminosilicate zeolite having a framework;
dealuminating the zeolite to remove aluminum atoms therefrom to produce a dealuminated framework comprising a plurality of vacancy sites;
contacting the dealuminated framework with a solvent that does not form hydrogen bonds with hydroxyl groups, and a precursor comprising heteroatoms selected from the group consisting of Sn, Ti, Zr, Hf, Pb, B, Ga, Fe, Be, Ge, V, Nb, Ta, Cr, Co, and Cu; and then
heating the dealuminated framework, the solvent, and the precursor under reflux conditions to incorporate the heteroatoms into at least some of the plurality of vacancy sites in the dealuminated framework to produce a zeotype material having a zeolitic framework comprising the heteroatoms.

2. The process of claim 1, wherein the solvent is a polar aprotic solvent.

3. The process of claim 1, wherein the heteroatoms are Sn or Ti.

4. The process of claim 1, wherein the framework of the zeolite has a Beta topology.

5. The process of claim 1, wherein the heteroatoms are incorporated into more than ninety percent of the plurality of vacancy sites in the dealuminated framework during the heating step.

6. The process of claim 1, wherein each of the plurality of vacancies that incorporates one of the heteroatoms is a heteroatom site having an open configuration or a closed configuration, and relative amounts of heteroatoms sites having open and closed configurations in the zeotype material are controlled by controlling a fraction of the vacancy sites to which the heteroatoms are incorporated into during the heating step.

7. The process of claim 6, further comprising using the zeotype material as a catalyst in a reaction in which the overall number of heteroatom sites having an open or closed configuration affects the catalytic behavior.

8. The process of claim 1, wherein the solvent is dichloromethane.

9. The process of claim 1, wherein a fraction of the vacancy sites to which the heteroatoms are incorporated into during the heating step controls a desired Si-to-metal atom ratio of the zeotype material.

10. The process of claim 1, wherein the dealuminating step includes contacting the zeolite with nitric acid.

11. The process of claim 1, further comprising synthesizing the zeolite in a fluoride media to decrease the density of the vacancy sites in the zeotype material.

12. The process of claim 1, further comprising performing isomerization of glucose-to-fructose in the presence of the zeotype material.

13. The process of claim 12, further comprising controlling the heteroatom content in the zeotype material in order to improve a rate of isomerization.

14. The process of claim 13, wherein the heteroatom content is controlled by synthesizing the zeolite in a fluoride media to decrease the density of the vacancy sites in the zeotype material.

15. The zeotype material produced by the process of claim 1.

16. A process comprising:
dealuminating an aluminosilicate zeolite to remove aluminum atoms therefrom to produce a zeolitic framework comprising a plurality of vacancy sites; and
heating under reflux conditions the zeolitic framework, a solvent that does not form hydrogen bonds with hydroxyl groups, and a precursor to incorporate Sn atoms into at least some of the plurality of vacancy sites in the zeolitic framework to produce stannosilicate;
wherein the Sn atoms form Sn sites in the zeolitic framework and relative amounts of the Sn sites having open and closed configurations in the stannosilicate are controlled by controlling a fraction of the vacancy sites to which the Sn atoms are incorporated into during the heating step.

17. The process of claim 16, further comprising using the stannosilicate as a catalyst in a reaction in which the overall number of heteroatom sites having an open or closed configuration affects the catalytic behavior.

18. The process of claim 16, further comprising performing isomerization of glucose-to-fructose in the presence of the stannosilicate and controlling the heteroatom content in the stannosilicate in order to improve a rate of isomerization.

19. The process of claim 16, wherein the solvent is a polar aprotic solvent.

20. The stannosilicate produced by the process of claim 16.

* * * * *